US011202855B2

(12) United States Patent
Young et al.

(10) Patent No.: US 11,202,855 B2
(45) Date of Patent: Dec. 21, 2021

(54) METHODS FOR REMOVAL OF TOXINS FROM BLOOD USING AN EXTRACORPOREAL CIRCUIT COMPRISED OF A HOLLOW-FIBER FILTER MODULE AND POLYMER SORBENT IN COMBINATION

(71) Applicant: CYTOSORBENTS CORPORATION, Monmouth Junction, NJ (US)

(72) Inventors: Wei-Tai Young, Hillsborough, NJ (US); Tamaz Guliashvili, Philadelphia, PA (US); Andrew Scheirer, Bethlehem, PA (US); Josh Vichare, New Brunswick, NJ (US); Timothy Kovacs, Allentown, PA (US); Maryann Gruda, Yardley, PA (US); Thomas Golobish, Princeton, NJ (US); Vincent Capponi, Monmouth Junction, NJ (US); Phillip Chan, Cherry Hill, NJ (US)

(73) Assignee: CYTOSORBENTS CORPORATION, Monmouth Junction, NJ (US)

( * ) Notice: Subject to any disclaimer, the term of this patent is extended or adjusted under 35 U.S.C. 154(b) by 130 days.

(21) Appl. No.: 16/497,982

(22) PCT Filed: Mar. 22, 2018

(86) PCT No.: PCT/US2018/023705
§ 371 (c)(1),
(2) Date: Sep. 26, 2019

(87) PCT Pub. No.: WO2018/183072
PCT Pub. Date: Oct. 4, 2018

(65) Prior Publication Data
US 2021/0106743 A1 Apr. 15, 2021

Related U.S. Application Data

(60) Provisional application No. 62/477,075, filed on Mar. 27, 2017.

(51) Int. Cl.
*A61M 1/34* (2006.01)
*A61M 1/36* (2006.01)

(52) U.S. Cl.
CPC ........ *A61M 1/3486* (2014.02); *A61M 1/3475* (2014.02); *A61M 1/3663* (2013.01)

(58) Field of Classification Search
CPC ........ B01D 2311/06; B01D 2311/2623; B01D 2311/2626; B01D 2313/40; B01D 61/18;
(Continued)

(56) References Cited

U.S. PATENT DOCUMENTS

| 4,013,564 A | 3/1977 | Nose |
| 6,287,516 B1 | 9/2001 | Matson et al. |

(Continued)

FOREIGN PATENT DOCUMENTS

| EP | 0073888 A1 | 3/1983 |
| WO | WO 1995/004559 A1 | 2/1995 |

(Continued)

OTHER PUBLICATIONS

European Patent Application No. 18777490.6; Extended Search Report; dated Dec. 9, 2020; 15 pages.

*Primary Examiner* — Terry K Cecil
(74) *Attorney, Agent, or Firm* — BakerHostetler

(57) ABSTRACT

This invention discloses methods for reducing physiologic molecules in abnormal levels and/or exogenous toxins in blood from blood by way of an extracorporeal circuit comprising a hollow-fiber filter module and polymer sorbent in combination.

13 Claims, 8 Drawing Sheets

(58) Field of Classification Search
CPC .... B01D 63/02; B01D 63/046; A61M 1/3475;
A61M 1/3486; A61M 1/3663
See application file for complete search history.

(56) References Cited

U.S. PATENT DOCUMENTS

| | | | |
|---|---|---|---|
| 9,707,332 B2* | 7/2017 | Cho | A61M 1/16 |
| 2011/0218512 A1* | 9/2011 | Tullis | A61M 1/3472 604/500 |
| 2013/0248450 A1 | 9/2013 | Kenley et al. | |
| 2014/0284274 A1 | 9/2014 | Nilsson | |

FOREIGN PATENT DOCUMENTS

| | | |
|---|---|---|
| WO | WO 2006/012885 A1 | 2/2006 |
| WO | WO 2012/142180 A1 | 10/2012 |
| WO | WO 2014/079680 A1 | 5/2014 |

* cited by examiner

METHODS FOR REMOVAL OF TOXINS FROM BLOOD USING AN EXTRACORPOREAL CIRCUIT COMPRISED OF A HOLLOW-FIBER FILTER MODULE AND POLYMER SORBENT IN COMBINATION

CROSS-REFERENCE TO RELATED APPLICATIONS

This application is the National Stage Application of International Patent Application No. PCT/US2018/023705 filed Mar. 22, 2018 which claims priority to U.S. Provisional Patent Application No. 62/477,075, filed on Mar. 27, 2017, the disclosures of which are incorporated herein in its entirety.

GOVERNMENT RIGHTS

The subject matter disclosed herein was made with government support under contract number W81XWH-12-C-0038, awarded by the United States Army Medical Research and Materiel Command (USAMRMC). The government has certain rights in the herein disclosed subject matter.

TECHNICAL FIELD

The disclosed inventions are in the field of hemofiltration. The disclosed inventions are also in the field of reducing physiologic molecules in abnormal levels and/or exogenous toxins in blood.

BACKGROUND OF THE INVENTION

In U.S. Pat. No. 6,287,516 B1, entitled "Hemofiltration Systems, Methods, and Devices Used to Treat Inflammatory Mediator Disease," Matson et al. describe a hemofiltration system comprised of a hemofilter and an adsorbent device. Kenley et al. disclose a similar concept in US 2013/0248450 A1, entitled "Recirculating Fluid Filtration System." The inventions described by Kenley et al. are classified more broadly as fluid filtration systems, but in some embodiments are specified for removal of harmful substances from blood. Both patents describe a method in which a hemofilter and adsorbent device are used in conjunction to remove harmful substances from blood; however, methods described in both patents rely on the use of at least two separate pumps, one for the circulation of blood and at least one additional pump for the circulation of permeate.

SUMMARY OF THE INVENTION

This invention discloses methods for removal of physiologic molecules in abnormal levels and/or exogenous toxins from blood and blood products by way of an extracorporeal circuit comprising a hollow-fiber filter module and polymer sorbent. Physiologic molecules or ions in abnormal levels and/or exogenous toxins may include potassium ions, lactate, myoglobin, cytokines, viral pathogens, endotoxins, mycotoxins, and $\beta_2$ microglobulin, among others and therefore disclosed methods are useful for treating hyperkalemia, systemic inflammation, excessive levels of pro-inflammatory or anti-inflammatory stimulators or mediators, and rhabdomyolysis. The disclosed invention utilizes a combination of a hollow-fiber filter module and polymer sorbent in an extracorporeal circuit with a pump, and allows for the treatment of blood using polymer sorbents.

As blood enters the hollow-fiber filter module, blood cells pass through the internal channels of the fiber membranes while smaller molecules are able to permeate through the filter membranes and into the extraluminal space of the housing.

Several configurations are described herein, all of which include hollow-fiber filter module permeate coming in contact with a polymer sorbent, which selectively binds the one or both of physiologic molecules and physiologic ions in abnormal levels and/or exogenous toxins.

Compared with standard dialysis procedures, the disclosed methods does not use dialysate for convection of molecules targeted for removal, helping to greatly reduce the complexity associated with standard dialysis machines and procedures.

Compared with similar existing technologies, the methods described herein offer a major advantage in that only one pump is required for effective reduction of target molecules. Typically, methods utilizing a hollow-fiber filter module in combination with a polymer sorbent require one pump to circulate the blood through the hollow-fibers and at least one separate pump to generate flow of the permeate so that removal of target molecules is sufficient.

BRIEF DESCRIPTION OF THE DRAWINGS

The accompanying drawings, which are included to provide a further understanding of the disclosure, are incorporated in and constitute a part of this specification, illustrate aspects of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

DETAILED DESCRIPTION OF THE INVENTION

Figure 1:
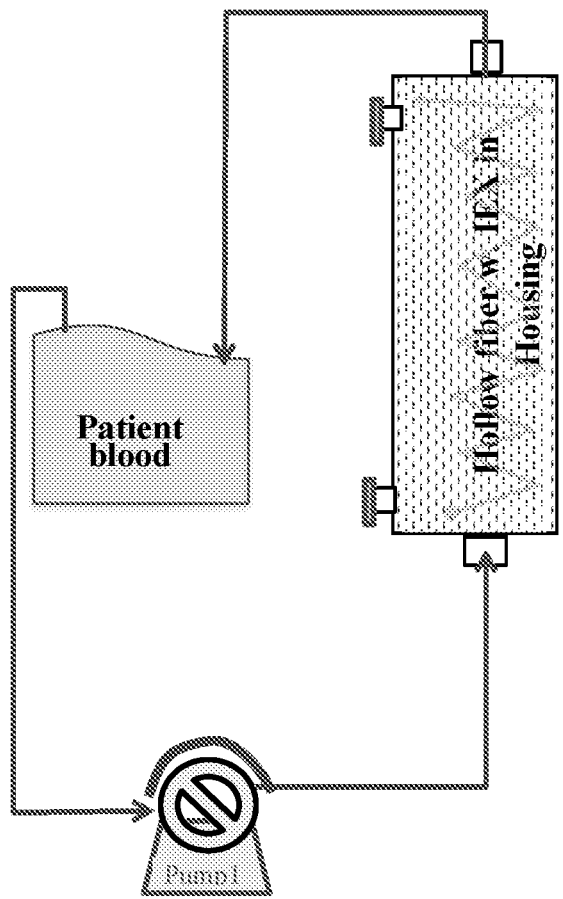
FIG. 1 is a schematic of an extracorporeal circuit utilizing a hollow-fiber filter module containing polymer sorbent in the extraluminal space of the housing.

As required, detailed embodiments of the present invention are disclosed herein; it is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the invention to be better understood. However, they are given merely by way of guidance and do not imply any limitation.

The present invention may be understood more readily by reference to the following detailed description taken in connection with the accompanying figures and examples, which form a part of this disclosure. It is to be understood that this invention is not limited to the specific materials, devices, methods, applications, conditions or parameters described and/or shown herein, and that the terminology used herein is for the purpose of describing particular embodiments by way of example only and is not intended to be limiting of the claimed invention. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention, which are, for clarity, described herein in the context of separate embodiments, may also be provided in combination in a single embodiment. Conversely, various features of the invention that are, for brevity, described in the context of a single embodiment, may also be provided separately or in any subcombination. Further reference to values stated in ranges includes each and every value and combination of values within that range.

The following definitions are intended to assist in understanding the present invention:

As used herein, the term "sorbent" includes adsorbents and ion exchange media.

For purposes of this invention, the term "sorb" is defined as "taking up and binding by absorption, adsorption or ion exchange".

The term "permeate" describes the components of blood that have passed through hollow-fiber membranes from the lumen into the extraluminal space. The term "extraluminal port" means a circuit connector for permeate flow in or out of the extraluminal space. The term "luminal port" means a circuit connector for blood flow in or out through the hollow fibers in a hollow fiber module.

As used herein, the phrase "one pump" in our application can be interpreted as "one pumping channel."

The treatment method described herein includes three major components; a polymer sorbent, a hollow-fiber filter module, and an extracorporeal circuit.

The polymer sorbent may be prepared by any means known in the art to produce a suitable polymer. Polymers may be porous or nonporous, and polymer sorbents may be selected based on their properties for targeted removal of a given molecule. For example, polymers useful for the methods described herein may include cytokine adsorbers, ion exchangers, mycotoxin adsorbers, endotoxin adsorbers, and polymers functionalized with ligands or aptamers for more specific molecular target binding. Polymer sorbent may be filled within the extraluminal space of a hollow-fiber filter module, or contained in a separate device.

The hollow-fiber filter module consists of biocompatible hollow-fiber membranes extending the length of the module such that open ends of fibers are only exposed to endcaps, and the seal holding the hollow-fibers in place creates an extraluminal compartment within the module housing. There are two extraluminal ports to the extraluminal compartment to allow for tangential flow filtration. As whole blood enters the module, cells and larger molecules pass straight through the fibers while smaller molecules are able to pass through the semi-permeable membranes and enter the extraluminal space as permeate. Hollow-fibers having different properties, such as membrane material, membrane area, and membrane molecular cutoff, can be selected depending on the molecules targeted for removal. Additionally, the configuration of the hollow-fibers within the module can be modified to alter the filter performance efficiency. Some commercially available hollow-fiber modules that may be useful for the methods described herein may include hemodialysis dialyzer, concentrator, ultra-filtration, and those used in bioprocessing.

The extracorporeal circuit comprises a minimum of a blood line set and blood pump to completely circulate blood from a patient, through lumens of the hollow-fibers, and back to the patient. Certain embodiments described herein utilize additional features within the extracorporeal circuit to improve efficiency, capacity, selectivity, or a combination thereof.

In some embodiments, the extracorporeal circuit utilizes a combination of a hollow-fiber filter module and polymer sorbent wherein polymer sorbent is located in the extraluminal space within the housing compartment of the hollow-fiber filter module. The polymer sorbent is retained by screens at both of the extraluminal ports. Blood is pumped through hollow-fibers while physiologic molecules in abnormal levels and/or exogenous toxins pass through the semi-permeable membrane of said hollow-fibers into the permeate and are retained by said polymer sorbent.

In some other embodiments, a line connecting one or both of the extraluminal ports of the hollow-fiber filter module housing to the inlet side of the blood pump is included to improve circulation of the permeate. Suction generated by the pump draws permeate from the extraluminal space and reintroduces it into blood at the inlet side of the blood pump. The circulation of the permeate improves the efficiency of the polymer sorbent in reducing physiologic molecules in abnormal levels and/or exogenous toxins in the blood.

In some embodiments, a line connecting one or both of the extraluminal ports of the hollow-fiber filter module to the blood return line is included to improve circulation of the permeate. Increased pressure in the extraluminal space compared with the blood return line will create a pressure gradient that drives permeate flow. The circulation of the permeate improves the efficiency of the polymer sorbent in reducing physiologic molecules in abnormal levels and/or exogenous toxins in the blood.

In other embodiments, permeate is recirculated through the extraluminal space of the hollow-fiber filter module by a second pump. The circulation of the permeate improves the efficiency of the polymer sorbent in reducing physiologic molecules in abnormal levels and/or exogenous toxins in the blood.

In other embodiments, permeate is recirculated through the extraluminal space of the hollow-fiber filter module by a thermosiphon circuit. A segment of highly conductive tubing is included in a line from the extraluminal space outlet to the extraluminal space inlet. Exposure to air causes a temperature decrease in the permeate inside the conductive tubing segment, creating a thermal gradient with the warmer permeate inside the extraluminal space of the housing. The thermal gradient induces circulation of the permeate, as colder fluid sinks down the thermosiphon circuit. The circulation of the permeate improves the efficiency of the polymer sorbent in reducing physiologic molecules in abnormal levels and/or exogenous toxins in the blood.

In some embodiments, the extracorporeal circuit utilizes a combination of a hollow-fiber filter module and polymer sorbent wherein polymer sorbent is located in a separate device housing than the hollow-fiber filter module. The separate polymer sorbent devices consist of a packed bead bed of the polymer beads in a flow-through container fitted with either a retainer screen at both the exit end and the entrance end to maintain the bead bed inside the container, or with a subsequent retainer screen to collect the beads after mixing. A line connects one or both of the extraluminal ports of the hollow-fiber filter module to the inlet of the separate polymer sorbent device housing, and another line connects the outlet of the separate polymer sorbent device housing to the inlet side of the blood pump. Blood is pumped through hollow-fibers while physiologic molecules in abnormal levels and/or exogenous toxins pass through the semi-permeable membrane of said hollow-fibers into the permeate. Suction generated by the pump draws permeate from the extraluminal space, pulls it through the separate polymer sorbent device housing, and reintroduces it into blood at the inlet side of the blood pump. Physiologic molecules in abnormal levels and/or exogenous toxins are retained by the polymer sorbent as the permeate passes through the polymer sorbent device housing.

In some embodiments, the extracorporeal circuit utilizes a combination of a hollow-fiber filter module and polymer sorbent wherein polymer sorbent is located in a separate device housing than the hollow-fiber filter module. The separate polymer sorbent devices consist of a packed bead bed of the polymer beads in a flow-through container fitted with either a retainer screen at both the exit end and the entrance end to maintain the bead bed inside the container, or with a subsequent retainer screen to collect the beads after mixing. Blood is pumped through hollow-fibers while physiologic molecules in abnormal levels and/or exogenous toxins pass through the semi-permeable membrane of said hollow-fibers into the permeate. Simultaneously, a second pump circulates permeate from the extraluminal space, through the separate polymer sorbent device, and back into the extraluminal space.

In some embodiments, multiple hollow-fiber filter modules containing polymer sorbent in the extraluminal space within the housing compartment are used in conjunction. The use of more than one of the same type of hollow-fiber filter modules could improve the capacity for removal of physiologic molecules in abnormal levels and/or exogenous toxins. Furthermore, the use of different types of hollow-fiber filter modules could be strategically employed to achieve removal of physiologic molecules in abnormal levels and/or exogenous toxins having vastly different molecular weight ranges. This could be accomplished by changing the type of hollow-fiber membrane, molecular weight cutoff of the hollow-fiber membrane, the polymer sorbent contained within the extraluminal space of the housing compartment, or any combination thereof. For example, using a first hollow-fiber only filter module having hollow fibers with a 10 kDa molecular cutoff to separate molecules smaller than 10 kDA, followed by a second module with polymer sorbent and hollow-fibers with a 25 kDa molecular cutoff would allow for treatment of the molecules in the 10 to 25 kDa range with polymer sorbent while the molecules smaller than 10 kDa can treated by another type of polymer sorbent or can be returned to the blood untreated.

In some other embodiments where the polymer sorbent is located in a separate device housing than the hollow-fiber filter module, multiple separate polymer sorbent devices are used in conjunction. The use of more than one of the same type of polymer sorbent device could improve the capacity for removal of physiologic molecules in abnormal levels and/or exogenous toxins. Furthermore, the use of different types of polymer sorbents could be strategically employed to remove physiologic molecules in abnormal levels and/or exogenous toxins having vastly different molecular weight ranges.

In some embodiments, a the use of a flow restriction instrument or regulator, such as a roller clamp, is included in the extracorporeal circuit to limit the flow rate of blood at the outlet of the hollow-fiber filter module and thereby increase the molecular permeation from the lumen of the hollow-fibers.

In some embodiments, the inclusion of one or more separate adsorption filters in the extracorporeal circuits with the hollow-fiber filter module and polymer sorbent combination can be utilized to further treat the blood. Adsorption filters may include activated charcoal, leptin adsorption filters, cytokine filters, or endotoxin filters.

In some embodiments concern methods for reducing (i) one or both of physiologic molecules and physiologic ions present in abnormal levels in blood and/or (ii) exogenous toxins in blood, utilizing a combination of a hollow-fiber filter module and polymer sorbent in an extracorporeal circuit; wherein:

the hollow-fiber module having (a) an extraluminal space within a housing compartment and (b) a plurality of hollow fibers and (c) at least two luminal ports which are configured to transport blood in and out through the hollow-fibers in the module and (d) at least one extraluminal port for transporting permeate from the hollow-fiber module; wherein:

the hollow fibers comprising semi-permeable membrane;

the polymer sorbent is located within a separate device housing with an inlet and an outlet ports for permeate flow through;

the inlet port of the sorbent device is connect to an extraluminal port of the hollow-fiber filter module and the outlet port of the sorbent device is connected to the inlet (suction) side of the blood pump of the extracorporeal circuit; the blood is pumped through the hollow-fibers while blood components comprising the one or both of physiologic molecules and physiologic ions present in abnormal levels and/or exogenous toxins pass through the semi-permeable membrane of the hollow-fibers into permeate, and the permeate is drawn from one or more extraluminal ports of the module, through the separate device containing the polymer sorbent, and at least a portion of the one or both of physiologic molecules and physiologic ions present in abnormal levels and/or exogenous toxins are retained by the polymer sorbent, and wherein the permeate pass through the sorbent device is reintroduced into the extracorporeal circuit at the inlet (suction) side of the blood pump which is the only pump used in the circuit including the luminal and permeate circuits.

The following examples are intended to be exemplary and non-limiting.

Example 1: (Run #28)

The general description and the following detailed description are exemplary and explanatory only and are not restrictive of the invention, as defined in the appended claims. Other aspects of the present invention will be apparent to those skilled in the art in view of the detailed description of the invention as provided herein.

A hollow-fiber filter module (P-CYTO09-06-N, Spectrum Labs) was filled with about 315 mL polymer sorbent (CY16195, CytoSorbents), such that the polymer sorbent occupied the housing space surrounding the hollow fibers and both of the extraluminal ports were closed off. This combination device was installed in a simple dynamic recirculation system with a blood pump (Fresenius Medical) and standard blood tubing set (SL2000M2095, Medisystem). A schematic of the experimental setup can be found below in FIG. 1. The entire recirculation loop was primed with saline solution, and then flushed with an additional 1 L saline solution.

4 L whole bovine blood (Lampire Biological Laboratory) was determined to have an initial potassium ($K^+$) concentration of 4.4 mEq/L. A bolus of 11.0 mEq $K^+$, from an aqueous solution having a concentration of 1126 mEq/L, was charged into the blood and mixed to achieve a measured blood concentration of 8.0 mEq/L. The reservoir bag was maintained at 37° C. using a thermal blanket and gently mixed using an orbital mixer throughout the experiment.

At time t=0, the blood pump was set to 350 mL/min. Simultaneously a separate infusion pump began infusing 0.5 mEq/min $K^+$, from an aqueous solution having a concentration of 1126 mEq/L, into the blood line between the combination device outlet and blood reservoir, until an additional total of 30.7 mEq $K^+$ was infused.

Blood continued to recirculate through the combination device for a total of 6 hours, with samples collected each hour. Results are presented below, in Table I. 27.4 mEq $K^+$ was removed by the polymer sorbent after 6 hours, corresponding to final blood potassium concentration of 8.8 mEq/L compared to the theoretical value of 14.8 mEq/L expected without treatment. The hemoglobin (Hb) concentration decreased by approximately 10% throughout the duration of the experiment as an artifact of priming the recirculation loop with saline, which contributed approximately 400 mL saline to the 4 L bovine blood.

TABLE I

Example 1 Results. Module has fibers in 8 bundles.

| Sample Time, Hours | Hb, g/L | $K^+$, mEq/L | $Na^+$, mEq/L | $Ca^{2+}$, mEq/L | $Cl^-$, mEq/L | $K^+$ Adsorbed on Polymer |
|---|---|---|---|---|---|---|
| Initial blood | 100 | 4.4 | 139 | 2.45 | 97 | N/A |
| 0 | 100 | 8 | 138 | 2.41 | 100 | 0 |
| 1 | 93 | 10.8 | 141 | 2.32 | 114 | 21.5 |
| 2 | 91 | 9.9 | 143 | 2.34 | 114 | 24.3 |
| 3 | 90 | 9.5 | 143 | 2.34 | 114 | 25.4 |
| 4 | 90 | 9.2 | 144 | 2.33 | 115 | 26.3 |
| 5 | 92 | 9.1 | 144 | 2.34 | 115 | 26.4 |
| 6 | 90 | 8.8 | 144 | 2.35 | 114 | 27.4 |

Example 2: (Run #32)

The general description and the following detailed description are exemplary and explanatory only and are not restrictive of the invention, as defined in the appended claims. Other aspects of the present invention will be apparent to those skilled in the art in view of the detailed description of the invention as provided herein.

Figure 2:
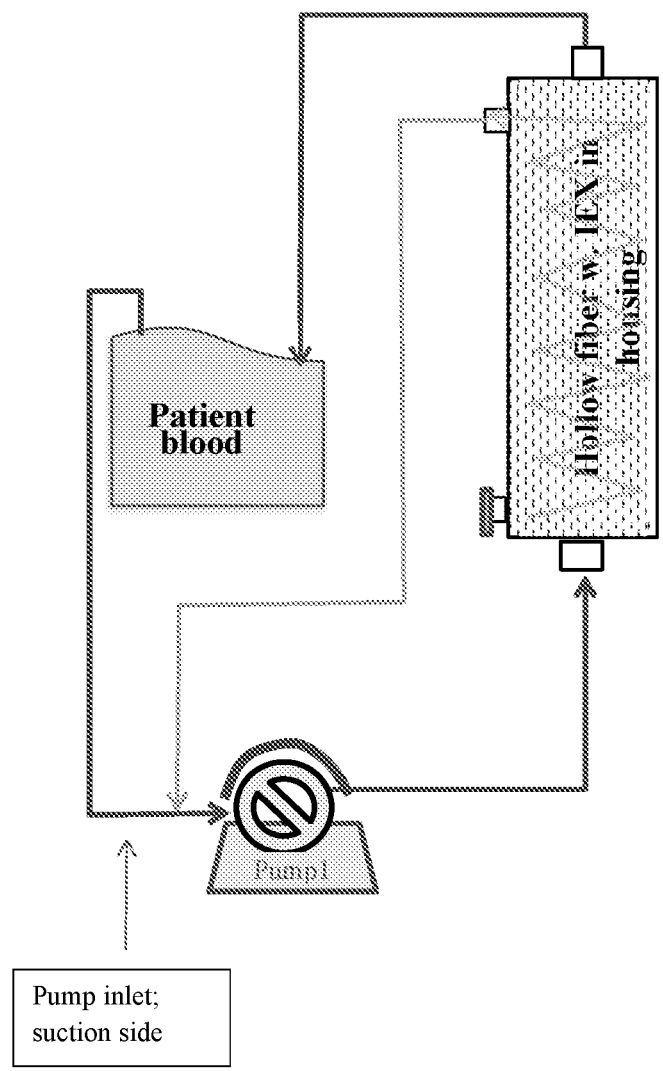
FIG. 2 is a schematic of an extracorporeal circuit utilizing a hollow-fiber filter module containing polymer sorbent in the extraluminal space of the housing, and an additional line connecting an extraluminal port of the extraluminal space housing to the inlet side of the blood pump.

A hollow-fiber filter module (P-CYTO09-05-N, Spectrum Labs) was filled with about 370 mL polymer sorbent (CY16195, CytoSorbents), such that the polymer sorbent occupied the housing space surrounding the hollow fibers. This combination device was installed in a dynamic recirculation system with a blood pump (Fresenius Medical) and standard blood tubing set (SL2000M2095, Medisystem). One of the extraluminal ports was closed off and the other was connected to the pump inlet line. A schematic of the experimental setup can be found below in FIG. 2. The entire recirculation loop was primed with saline solution, and then flushed with an additional 1 L saline solution.

4 L whole bovine blood (Lampire Biological Laboratory) was determined to have an initial potassium ($K^+$) concentration of 4.0 mEq/L. A bolus of 9.6 mEq $K^+$, from an aqueous solution having a concentration of 1123 mEq/L, was charged into the blood and mixed to achieve a measured blood concentration of 8.0 mEq/L. The reservoir bag was maintained at 37° C. using a thermal blanket and gently mixed using an orbital mixer throughout the experiment.

At time t=0, the blood pump was set to 350 mL/min. Simultaneously a separate infusion pump began infusing 0.5 mEq/min $K^+$, from an aqueous solution having a concentration of 1123 mEq/L, into the blood line between the combination device outlet and blood reservoir, until an additional total of 30.7 mEq $K^+$ was infused.

Blood continued to recirculate through the combination device for a total of 6 hours, with samples collected each hour. Results are presented below, in Table II. 32.1 mEq $K^+$ was removed by the polymer sorbent after 6 hours, corresponding to final blood potassium concentration of 7.5 mEq/L compared to the theoretical value of 14.6 mEq/L expected without treatment. The hemoglobin (Hb) concentration decreased by approximately 10% throughout the duration of the experiment as an artifact of priming the recirculation loop with saline, which contributed approximately 400 mL saline to the 4 L bovine blood.

TABLE II

Example 2 Results. Module has fibers in 4 bundles.

| Sample Time, Hours | Hb, g/L | $K^+$, mEq/L | $Na^+$, mEq/L | $Ca^{2+}$, mEq/L | $Cl^-$, mEq/L | $K^+$ Adsorbed on Polymer |
|---|---|---|---|---|---|---|
| Initial blood | 143 | 4.0 | 139 | 2.35 | 97 | N/A |
| 0 | 143 | 8.0 | 136 | 2.32 | 102 | 0.00 |
| 1 | 134 | 11.7 | 139 | 2.29 | 114 | 22.8 |
| 2 | 135 | 9.9 | 142 | 2.35 | 114 | 27.1 |
| 3 | 135 | 8.7 | 143 | 2.37 | 114 | 28.9 |
| 4 | 134 | 8.0 | 144 | 2.36 | 113 | 31.5 |

TABLE II-continued

Example 2 Results. Module has fibers in 4 bundles.

| Sample Time, Hours | Hb, g/L | $K^+$, mEq/L | $Na^+$, mEq/L | $Ca^{2+}$, mEq/L | $Cl^-$, mEq/L | $K^+$ Adsorbed on Polymer |
|---|---|---|---|---|---|---|
| 5 | 133 | 7.9 | 144 | 2.37 | 113 | 31.1 |
| 6 | 133 | 7.5 | 145 | 2.37 | 113 | 32.1 |

Example 3: (Run #23)

The general description and the following detailed description are exemplary and explanatory only and are not restrictive of the invention, as defined in the appended claims. Other aspects of the present invention will be apparent to those skilled in the art in view of the detailed description of the invention as provided herein.

Figure 3:
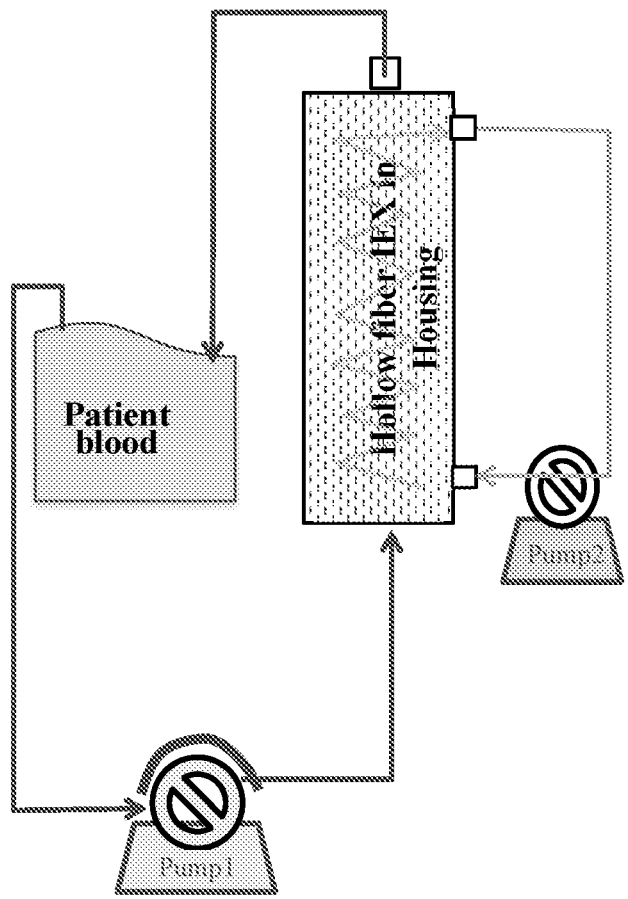
FIG. 3 is a schematic of an extracorporeal circuit utilizing a hollow-fiber filter module containing polymer sorbent in the extraluminal space of the housing, and a separate pump to circulate the permeate in the extraluminal space.

A hollow-fiber filter module (P-CYTO09-05-N, Spectrum Labs) was filled with about 345 mL polymer sorbent (CY16195, CytoSorbents), such that the polymer sorbent occupied the housing space surrounding the hollow fibers. This combination device was installed in a dynamic recirculation system with a blood pump (Fresenius Medical) and standard blood tubing set (SL2000M2095, Medisystem). A second pump and additional lines were installed to recirculate transmembrane fluid through the housing. A schematic of the experimental setup can be found below in FIG. 3. Both recirculation loops, blood and transmembrane fluid, were primed with saline solution, and then flushed with an additional 1 L saline solution.

4 L whole bovine blood (Lampire Biological Laboratory) was determined to have an initial potassium ($K^+$) concentration of 4.0 mEq/L. A bolus of 11.4 mEq $K^+$, from an aqueous solution having a concentration of 1126 mEq/L, was charged into the blood and mixed to achieve a measured blood concentration of 7.8 mEq/L. The reservoir bag was maintained at 37° C. using a thermal blanket and gently mixed using an orbital mixer throughout the experiment.

At time t=0, the blood pump was set to 350 mL/min. Simultaneously a separate infusion pump began infusing 0.5 mEq/min $K^+$, from an aqueous solution having a concentration of 1126 mEq/L, into the blood line between the combination device outlet and blood reservoir, until an additional total of 31.2 mEq $K^+$ was infused.

Blood continued to recirculate through the combination device for a total of 6 hours, with samples collected each hour. Results are presented below, in Table III. 36.4 mEq $K^+$ was removed by the polymer sorbent after 6 hours, corresponding to final blood potassium concentration of 4.9 mEq/L compared to the theoretical value of 14.6 mEq/L expected without treatment. The hemoglobin (Hb) concentration decreased by approximately 10% throughout the duration of the experiment as an artifact of priming the recirculation loop with saline, which contributed approximately 400 mL saline to the 4 L bovine blood.

TABLE III

Example 3 Results. Module has fibers in 4 bundles.

| Sample Time, Hours | Hb, g/L | $K^+$, mEq/L | $Na^+$, mEq/L | $Ca^{2+}$, mEq/L | $Cl^-$, mEq/L | $K^+$ Adsorbed on Polymer |
|---|---|---|---|---|---|---|
| Initial blood | 106 | 4.0 | 143 | 2.34 | 103 | N/A |
| 0 | 103 | 7.8 | 141 | 2.31 | 106 | 0.0 |
| 1 | 97 | 7.6 | 147 | 2.25 | 119 | 27.4 |
| 2 | 93 | 5.4 | 149 | 2.31 | 119 | 34.8 |
| 3 | 93 | 5.1 | 150 | 2.33 | 119 | 35.7 |
| 4 | 93 | 5.0 | 150 | 2.35 | 119 | 36.1 |
| 5 | 93 | 5.0 | 150 | 2.36 | 119 | 36.1 |
| 6 | 93 | 4.9 | 150 | 2.35 | 119 | 36.4 |

Example 4: (Run #20)

The general description and the following detailed description are exemplary and explanatory only and are not restrictive of the invention, as defined in the appended claims. Other aspects of the present invention will be apparent to those skilled in the art in view of the detailed description of the invention as provided herein.

Figure 4:
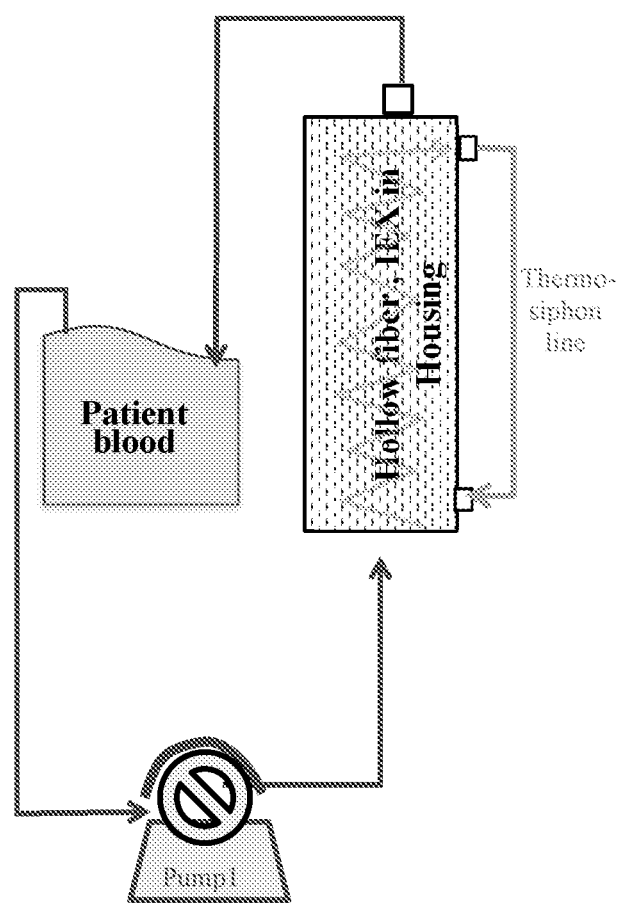
FIG. 4 is a schematic of an extracorporeal circuit utilizing a hollow-fiber filter module containing polymer sorbent in the extraluminal space of the housing, and a thermosiphon to circulate the permeate in the extraluminal space.

A hollow-fiber filter module (P-CYTO09-05-N, Spectrum Labs) was filled with about 375 mL polymer sorbent (CY16195, CytoSorbents), such that the polymer sorbent occupied the housing space surrounding the hollow fibers. This combination device was installed in a dynamic recirculation system with a blood pump (Fresenius Medical) and standard blood tubing set (SL2000M2095, Medisystem). An additional line containing a segment of highly conductive tubing was connected from the housing outlet to the housing inlet. The highly conductive tubing establishes a thermosiphon to help recirculate transmembrane fluid through the housing. A schematic of the experimental setup can be found below in FIG. 4. Both recirculation loops, blood and thermosiphon line, were primed with saline solution, and then flushed with an additional 1 L saline solution.

4 L whole bovine blood (Lampire Biological Laboratory) was determined to have an initial potassium ($K^+$) concentration of 4.5 mEq/L. A bolus of 9.6 mEq $K^+$, from an aqueous solution having a concentration of 1126 mEq/L, was charged into the blood and mixed to achieve a measured blood concentration of 7.7 mEq/L. The reservoir bag was maintained at 37° C. using a thermal blanket and gently mixed using an orbital mixer throughout the experiment.

At time t=0, the blood pump was set to 690 mL/min. Simultaneously a separate infusion pump began infusing 0.5 mEq/min $K^+$, from an aqueous solution having a concentration of 1126 mEq/L, into the blood line between the combination device outlet and blood reservoir, until an additional total of 33.0 mEq $K^+$ was infused.

Blood continued to recirculate through the combination device for a total of 6 hours, with samples collected each hour. Results are presented below, in Table IV. 28.9 mEq $K^+$ was removed by the polymer sorbent after 6 hours, corresponding to final blood potassium concentration of 8.2 mEq/L compared to the theoretical value of 15.1 mEq/L expected without treatment. The hemoglobin (Hb) concentration decreased by approximately 10% throughout the duration of the experiment as an artifact of priming the recirculation loop with saline, which contributed approximately 400 mL saline to the 4 L bovine blood.

TABLE IV

Example 4 Results. Module has fibers in 4 bundles.

| Sample Time, Hours | Hb, g/L | K$^+$, mEq/L | Na$^+$, mEq/L | Ca$^{2+}$, mEq/L | Cl$^-$, mEq/L | K$^+$ Adsorbed on Polymer |
|---|---|---|---|---|---|---|
| Initial blood | 124 | 4.5 | 142 | 2.39 | 103 | N/A |
| 0 | 123 | 7.7 | 141 | 2.37 | 104 | 0.0 |
| 1 | 111 | 6.5 | 137 | 2.11 | 108 | 14.8 |
| 2 | 113 | 7.6 | 141 | 2.16 | 111 | 20.0 |
| 3 | 113 | 9.2 | 141 | 2.17 | 114 | 26.0 |
| 4 | 112 | 8.6 | 141 | 2.2 | 113 | 27.8 |
| 5 | 113 | 8.4 | 142 | 2.22 | 113 | 28.3 |
| 6 | 113 | 8.2 | 142 | 2.21 | 112 | 28.9 |

TABLE V

Example 5 Results. Dialyzer has fibers in 1 bundle, polymer sorbent in separate device.

| Sample Time, Hours | Hb, g/L | K$^+$, mEq/L | Na$^+$, mEq/L | Ca$^{2+}$, mEq/L | Cl$^-$, mEq/L | K$^+$ Adsorbed on Polymer |
|---|---|---|---|---|---|---|
| Initial blood | 112 | 4.0 | 141 | 2.29 | 101 | N/A |
| 0 | 112 | 7.8 | 140 | 2.24 | 104 | 0.0 |
| 1 | 105 | 6.1 | 148 | 2.4 | 118 | 35.9 |
| 2 | 104 | 4.0 | 151 | 2.55 | 118 | 41.7 |
| 3 | 106 | 4.0 | 151 | 2.53 | 118 | 41.1 |
| 4 | 103 | 4.1 | 151 | 2.49 | 118 | 40.9 |
| 5 | 106 | 4.0 | 151 | 2.48 | 117 | 40.7 |
| 6 | 103 | 4.0 | 152 | 2.47 | 118 | 40.7 |

Example 5: (Run #40)

The general description and the following detailed description are exemplary and explanatory only and are not restrictive of the invention, as defined in the appended claims. Other aspects of the present invention will be apparent to those skilled in the art in view of the detailed description of the invention as provided herein.

Figure 5:
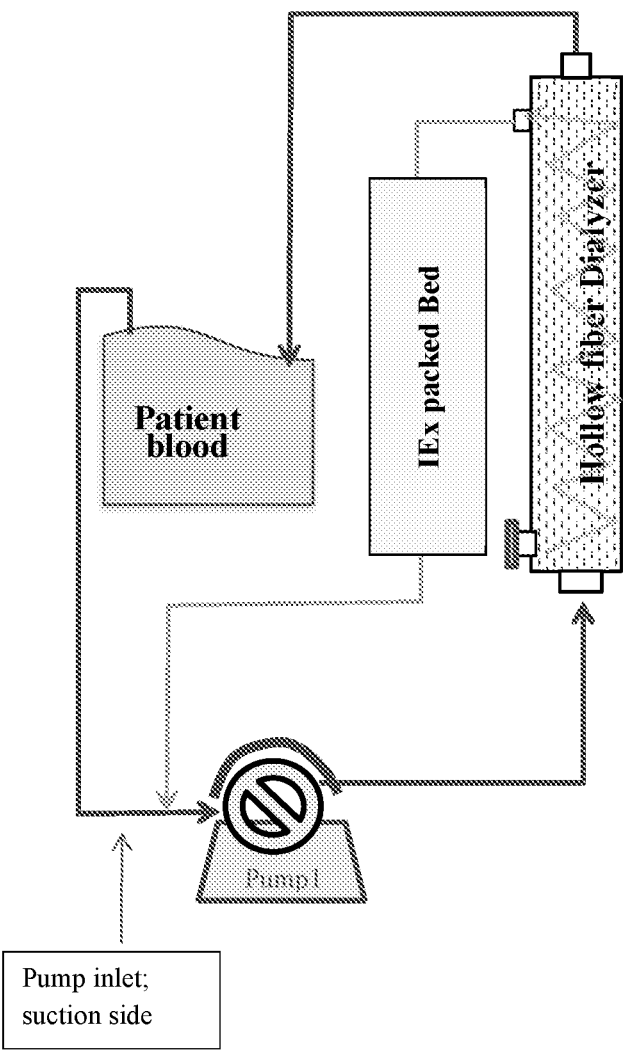
FIG. 5 is a schematic of an extracorporeal circuit utilizing a hollow-fiber filter module and a separate polymer sorbent device that is included in a line connecting an extraluminal port of the extraluminal space housing to the inlet side of the blood pump.

A hollow-fiber filter module (XPH-170, Baxter Healthcare) and a separate polymer sorbent device, filled with about 470 mL polymer sorbent (CY16195, CytoSorbents), were installed in a dynamic recirculation system with a blood pump (Fresenius Medical) and standard blood tubing set (SL2000M2095, Medisystem). One of the two extraluminal ports was closed off and the other was connected to the inlet of the polymer sorbent device, and an additional line was installed to connect the polymer sorbent device outlet to the blood pump inlet line. A schematic of the experimental setup can be found below in FIG. 5. The entire recirculation loop was primed with saline solution, and then flushed with an additional 2 L saline solution.

4 L whole bovine blood (Lampire Biological Laboratory) was determined to have an initial potassium (K$^+$) concentration of 4.0 mEq/L. A bolus of 11.4 mEq K$^+$, from an aqueous solution having a concentration of 1123 mEq/L, was charged into the blood and mixed to achieve a measured blood concentration of 7.8 mEq/L. The reservoir bag was maintained at 37° C. using a thermal blanket and gently mixed using an orbital mixer throughout the experiment.

At time t=0, the blood pump was set to 350 mL/min. Simultaneously a separate infusion pump began infusing 0.5 mEq/min K$^+$, from an aqueous solution having a concentration of 1123 mEq/L, into the blood line between the combination device outlet and blood reservoir, until an additional total of 31.4 mEq K$^+$ was infused.

Blood continued to recirculate through the hollow-fiber filter module for a total of 6 hours, with samples collected each hour. Results are presented below, in Table V. 40.7 mEq K$^+$ was removed by the polymer sorbent after 6 hours, corresponding to final blood potassium concentration of 4.0 mEq/L compared to the theoretical value of 14.7 mEq/L expected without treatment. The hemoglobin (Hb) concentration decreased by approximately 10% throughout the duration of the experiment as an artifact of priming the recirculation loop with saline, which contributed approximately 400 mL saline to the 4 L bovine blood.

Example 6: (Run #25)

The general description and the following detailed description are exemplary and explanatory only and are not restrictive of the invention, as defined in the appended claims. Other aspects of the present invention will be apparent to those skilled in the art in view of the detailed description of the invention as provided herein.

Figure 6:
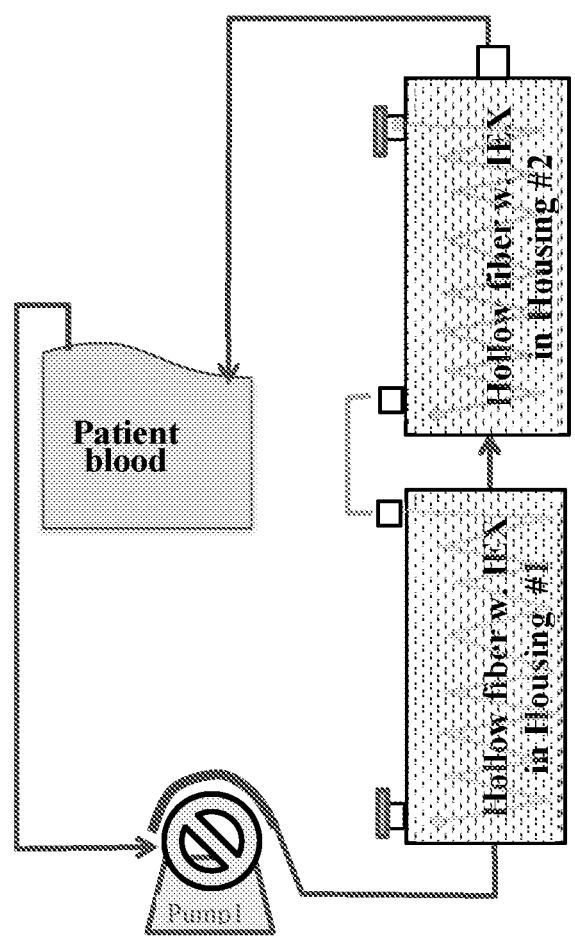
FIG. 6 is a schematic of an extracorporeal circuit utilizing two hollow-fiber filter modules in series, each containing polymer sorbent in the extraluminal space of the housing.
Figure 7:
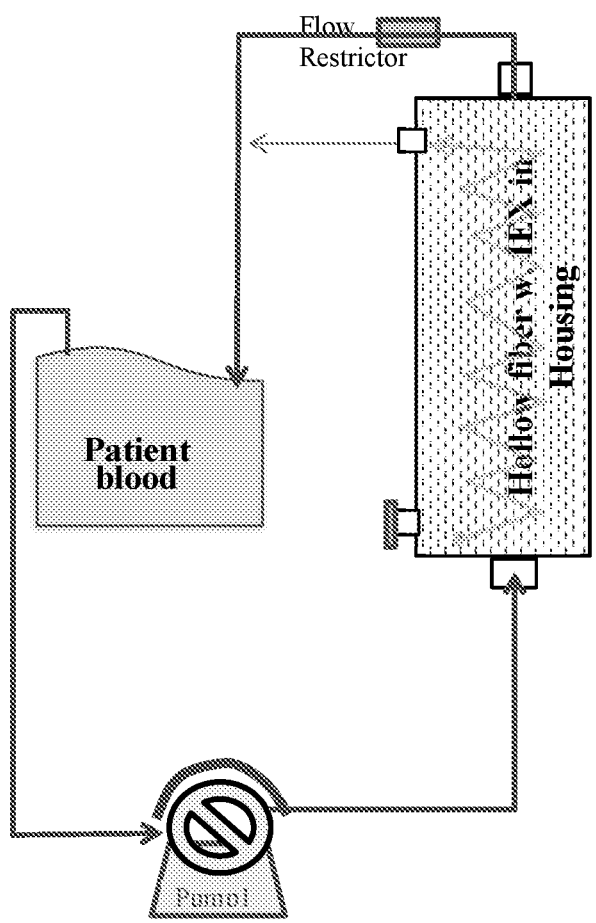
FIG. 7 is a schematic of an extracorporeal circuit utilizing a hollow-fiber filter module containing polymer sorbent in the extraluminal space of the housing, a flow restriction device at the blood outlet, and an additional line connecting an extraluminal port of the extraluminal space housing to the blood return line.
Figure 8:
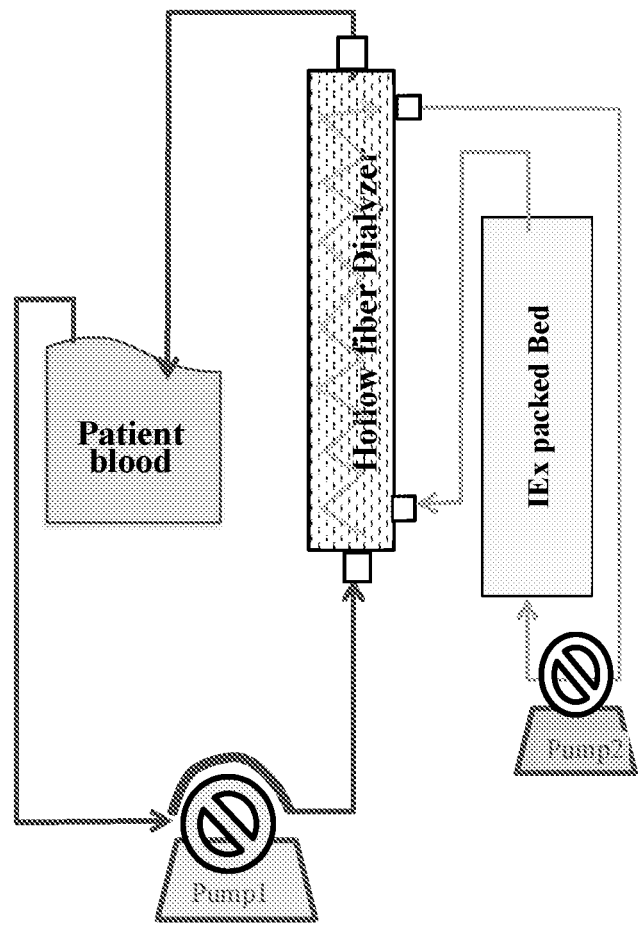
FIG. 8 is a schematic of an extracorporeal circuit utilizing a hollow-fiber filter module and a separate polymer sorbent device, with separate pumps for blood circulation and permeate circulation.

Two hollow-fiber filter module (P-CYTO09-06-N, Spectrum Labs) were each filled with about 330 mL polymer sorbent (CY16195, CytoSorbents), such that the polymer sorbent occupied the housing space surrounding the hollow fibers. These combination devices were installed in series in a simple dynamic recirculation system with a blood pump (Fresenius Medical) and standard blood tubing set (SL2000M2095, Medisystem). Additional line was used to connect the housing outlet of device 1 to the housing inlet of device 2. Both the housing inlet of device 1 and the housing outlet of device 2 were closed off. A schematic of the experimental setup can be found below in FIG. 6. The entire recirculation loop was primed with saline solution, and then flushed with an additional 1 L saline solution.

4 L whole bovine blood (Lampire Biological Laboratory) was determined to have an initial potassium (K$^+$) concentration of 3.7 mEq/L. A bolus of 13.3 mEq K$^+$, from an aqueous solution having a concentration of 1126 mEq/L, was charged into the blood and mixed to achieve a measured blood concentration of 8.4 mEq/L. The reservoir bag was maintained at 37° C. using a thermal blanket and gently mixed using an orbital mixer throughout the experiment.

At time t=0, the blood pump was set to 350 mL/min. Simultaneously a separate infusion pump began infusing 0.5 mEq/min K$^+$, from an aqueous solution having a concentration of 1126 mEq/L, into the blood line between the combination device outlet and blood reservoir, until an additional total of 30.0 mEq K$^+$ was infused.

Blood continued to recirculate through the hollow-fiber filter module for a total of 6 hours, with samples collected each hour. Results are presented below, in Table VI. 38.8 mEq K$^+$ was removed by the polymer sorbent after 6 hours, corresponding to final blood potassium concentration of 5.0 mEq/L compared to the theoretical value of 14.5 mEq/L expected without treatment. The hemoglobin (Hb) concentration decreased by approximately 10% throughout the duration of the experiment as an artifact of priming the recirculation loop with saline, which contributed approximately 400 mL saline to the 4 L bovine blood.

TABLE VI

Example 6 Results. Module has fibers in 8 bundles.

| Sample Time, Hours | Hb, g/L | $K^+$, mEq/L | $Na^+$, mEq/L | $Ca^{2+}$, mEq/L | $Cl^-$, mEq/L | $K^+$ Adsorbed on Polymer |
|---|---|---|---|---|---|---|
| Initial blood | 90 | 3.70 | 143 | 2.33 | 102 | N/A |
| 0 | 88 | 8.4 | 143 | 2.33 | 107 | 0.0 |
| 1 | 79 | 8.6 | 145 | 2.36 | 121 | 28.7 |
| 2 | 76 | 6.8 | 148 | 2.42 | 121 | 34.4 |
| 3 | 81 | 5.8 | 148 | 2.44 | 120 | 37.4 |
| 4 | 81 | 5.4 | 149 | 2.44 | 120 | 38.4 |
| 5 | 80 | 5.2 | 149 | 2.44 | 120 | 38.7 |
| 6 | 80 | 5.0 | 150 | 2.46 | 120 | 38.8 |

What is claimed:

1. A method for reducing (i) one of physiologic molecules and physiologic ions present in abnormal levels in blood and/or (ii) exogenous toxins in blood, the method comprising contacting the blood with a polymer sorbent in an extracorporeal circuit; wherein
said extracorporeal circuit comprises a hollow-fiber filter module having (a) an extraluminal space within a housing compartment and (b) a plurality of hollow fibers and (c) at least two luminal ports which are configured to transport blood in and out through said hollow fibers in said module; and (d) at least two extraluminal ports for flow in and out of said extraluminal space; wherein:
said hollow fibers comprising semi-permeable membranes;
said polymer sorbent is located in said extraluminal space within said housing compartment of said hollow-fiber filter module, and said polymer sorbent is retained in said extraluminal space by screens at said extraluminal ports of said hollow-fiber filter module;
said blood is pumped through said hollow fibers while blood components comprising said at least one of physiologic molecules and physiologic ions present in abnormal levels and/or exogenous toxins pass through the semi-permeable membranes of said hollow fibers into permeate within the extraluminal space and at least a portion of said at least one of physiologic molecules and physiologic ions present in abnormal levels and/or exogenous toxins are retained by said polymer sorbent; and
wherein said blood is pumped through said hollow fibers and said permeate is recirculated through the extraluminal space of said housing compartment by a single pump.

2. The method of claim 1, comprising drawing permeate from one or both extraluminal ports of said housing, and reintroducing the permeate into the extracorporeal circuit via an inlet (suction) side of the pump that recirculates the blood through the hollow fibers.

3. The method of claim 1, wherein the method utilizes multiple extracorporeal circuits and hollow-fiber filter modules.

4. The method of claim 3, comprising removing molecules of different molecular weight ranges or that contain different functional groups with different polymer sorbents and/or different hollow fibers.

5. The method of claim 3, comprising removing molecules of different molecular weight ranges or molecules of different types of chemical or structural types of molecules with multiple separate polymer sorbent containing devices in the extracorporeal circuits; wherein the separate polymer sorbent containing devices comprise different polymer sorbents.

6. The method of claim 1, comprising providing an additional tubing line from one or both extraluminal ports of the hollow-fiber filter module housing to a blood return line in the extracorporeal circuit to improve circulation of permeate.

7. The method of claim 6, wherein the plurality of hollow fibers are arranged into a configuration including one bundle, multiple bundles, dispersed in particular patterns, randomly dispersed, or any combination thereof.

8. The method claim 1, comprising providing a flow restriction instrument or regulator in the extracorporeal circuit to limit the flow rate of blood out one of the luminal ports of the hollow-fiber filter module and thereby increasing the molecular permeation from lumens of the hollow fibers.

9. The method of claim 8, wherein the flow restriction instrument is a roller clamp.

10. The method of claim 1, wherein one or more separate adsorption filters are used with the extracorporeal circuit, wherein the one or more separate adsorption filters include at least one of activated charcoal, leptin adsorption filters, endotoxin adsorption filters, and cytokine adsorption filters.

11. The method of claim 1, comprising providing at least one membrane for dialysis and bioprocessing.

12. A method for reducing (i) at least one of physiologic molecules and physiologic ions present in abnormal levels in blood and/or (ii) exogenous toxins in blood, the method comprising contacting the blood with a polymer sorbent in an extracorporeal circuit; wherein
said extracorporeal circuit comprises a hollow-fiber filter module having (a) an extraluminal space within a housing compartment and (b) a plurality of hollow fibers and (c) at least two luminal ports which are configured to transport blood in and out through said hollow fibers in said module and (d) at least one extraluminal port for transporting permeate from said hollow-fiber filter module; wherein:
said hollow fibers comprising semi-permeable membranes;
said polymer sorbent is located within a separate sorbent device housing with an inlet port and an outlet port for permeate flow therethrough; said inlet port of said sorbent device housing is connected to an extraluminal port of said hollow-fiber filter module and the outlet port of said sorbent device housing is connected to an inlet (suction) side of a blood pump of the extracorporeal circuit;
said blood is pumped through said hollow fibers while blood components comprising said at least one of physiologic molecules and physiologic ions present in abnormal levels and/or exogenous toxins pass through the semi-permeable membranes of said hollow fibers into permeate, and said permeate is drawn from said at least one extraluminal port of said module, through the separate sorbent device housing containing said polymer sorbent, and at least a portion of said at least one of physiologic molecules and physiologic ions present in abnormal levels and/or exogenous toxins are retained by said polymer sorbent, and
wherein said permeate passing through the sorbent device housing is reintroduced into the extracorporeal circuit at the inlet (suction) side of the blood pump which is the only pump used in the circuit; and wherein said blood is pumped through said hollow fibers and said permeate is recirculated through the extraluminal space of said housing compartment by a single pump: the blood pump.

13. A hollow-fiber filter module for reducing (i) at least one of physiologic molecules and physiologic ions present in abnormal levels in blood and/or (ii) exogenous toxins in blood, said module having (a) an extraluminal space within a housing compartment and (b) a plurality of hollow fibers; (c) at least two luminal housing ports which are configured to transport blood in and out through said hollow fibers in said module and at least two extraluminal housing ports which serve as circuit connectors for permeate flow in or out of the extraluminal space; wherein:

said hollow fibers comprising semi-permeable membranes;

a polymer sorbent is located in said extraluminal space within said housing compartment of said hollow-fiber filter module, and said polymer sorbent is retained in said extraluminal space by screens at said luminal and extraluminal housing ports of said hollow-fiber filter module;

said module configured with a single pump to allow blood to be pumped through said hollow fibers while blood components comprising said at least one of physiologic molecules and physiologic ions present in abnormal levels and/or exogenous toxins pass through the semi-permeable membrane of said hollow fibers into permeate within the extraluminal space and at least a portion of said at least one of physiologic molecules and physiologic ions present in abnormal levels and/or exogenous toxins are retained by said polymer sorbent; and wherein said blood is pumped through said hollow fibers and said permeate is recirculated through the extraluminal space of said housing compartment by the single pump.

* * * * *